United States Patent [19]

Seckel

[11] Patent Number: 5,584,885
[45] Date of Patent: Dec. 17, 1996

[54] NERVE REGENERATION CHAMBER

[76] Inventor: Brooke R. Seckel, 21 River St., Concord, Mass. 01747

[21] Appl. No.: 234,248

[22] Filed: Apr. 28, 1994

[51] Int. Cl.⁶ .............................. A61F 2/02; A01N 1/02; A61B 17/08
[52] U.S. Cl. .......................... 623/11; 435/1.2; 435/240.1; 435/284.1; 606/152
[58] Field of Search ...................................... 606/152, 153; 435/1, 240.22, 240.23, 284, 294; 424/422, 423; 623/11, 66

[56] References Cited

U.S. PATENT DOCUMENTS

| | | | |
|---|---|---|---|
| 3,786,817 | 1/1974 | Palma | 606/152 |
| 5,151,362 | 9/1992 | Kawaguchi et al. | 435/284 |
| 5,151,366 | 9/1992 | Serkes et al. | 435/284 |

OTHER PUBLICATIONS

Brooke Seckel, Nerve Regeneration through Synthethic Biodegradable Nerve Guides: Regulations by the Target Organ–Plastic and Reconstructive Surgery–Aug., 1984–pp. 173–181.

Brooke R. Seckel–Current Status of Peripheral Nerve Surgery–Perspectives in Plastic Surgery–vol. 4, No. 2, 1990, pp. 91–104.

*Primary Examiner*—Robert A. H. Clarke
*Attorney, Agent, or Firm*—Gary D. Clapp, Esq.

[57] ABSTRACT

A regeneration chamber for promoting and controlling the growth of biological nerves, including a chamber enclosing and defining a volume in which biological nerves are to be grown, an input port for injecting agents for promoting and controlling the growth of the biological nerves into the chamber, and an output port for receiving agents and biological nerve growth byproducts from the chamber. The input port and chamber have at least one input passage therebetween for the flow of agents from the input port into the chamber and the output port and chamber have at least one output passage therebetween for the flow of agents and biological growth byproducts from the chamber into the output port. The input and output passages are proportioned to reduce increases and decreases in pressure in the chamber and a chamber may have a plurality of input ports and output ports. The passages may be proportioned to the flow characteristics of certain agents, including by selection of the materials for the input and output ports. The regeneration chamber may include a plurality of chamber internal structures, including one or more surface matrices of agents disposed within the chamber or one or more sub-chambers and certain of the sub-chambers may be provided with input and output ports. The chamber internal structures may replicate selected internal biological structures of an organ to be grown.

6 Claims, 5 Drawing Sheets

NERVE REGENERATION CHAMBER

FIELD OF THE INVENTION

The present invention relates to a method and apparatus for regeneration of biological tissues and, in particular, to a method and apparatus for controlling a microenvironment for the regeneration of biological tissues.

BACKGROUND OF THE INVENTION

One of the major problems in current medical practice, and in particular in current reconstructive medicine, is the development of effective methods and apparatus for the healing, regeneration or repair of injured, damaged, destroyed or deficient biological tissues, such as nerve structures of the brain, spinal cord and peripheral nervous system, or for enhancing the normal regenerative or healing processes of such tissues.

The medical field has long recognized that many biological tissues have the capacity to regenerate themselves or to otherwise heal injuries through various mechanisms. It is widely known, however, that the ability of tissues to heal or regenerate varies widely among the various types of tissues and appears to be a balancing between the need for self repair to avoid further harm to the organism and the problems that could arise from faulty self repair. For example, in the human body the skin and bone tissues have a very strong capability for regeneration and healing to prevent blood loss and infection and to maintain the structural integrity of the body. The tissues of certain of the internal organs, such as the liver and lungs, have a lesser capability for self regeneration but the human body can function adequately with only a part of the liver or with one lung. The tissues of the nervous system have very little capability for self regeneration and healing but the problems arising from faulty self repair, such as a crossing between self regenerating motor and sensory nerves, are potentially more hazardous than the loss of the nervous functions.

In addition, it is recognized that while certain of the healing mechanisms, such as the development of scar tissue to replace original tissue, are biologically effective the replacement tissues are inferior to the original tissues. For example, the scar tissue that replaces original skin tissues functions adequately to prevent the loss of blood and to protect against infection but lacks the flexibility and sensory nerves of the original skin tissues and is aesthetically undesirable. In a like manner, the development of scar tissues in internal organs may restore the physical integrity of the internal organs but does not replicate the functions of the original organ tissues. In such instances, the replacement of the original tissues by the repair tissues is less desirable than would be the regeneration of the original tissues.

The techniques for repairing or reconstructing the internal organs, skin tissues and bone structures of the human body are relatively well known and highly developed but are not completely satisfactory. For example, damaged or deteriorated bone structures may be replaced with or supplemented with artificial constructs, such as artificial hip joints and pins to reinforce the bones, but the surrounding bone may fail to grow in around the artificial construct adequately or there may be extraneous bone growth. It is possible to replace internal organs with organs from donors or to implant artificial aids for certain organs, such as pacemakers and valves for the heart, but the replacement may cause undesirable reactions and the replacement or artificial aid cannot restore the complete original functionality of the organ. In a like manner, it is possible to surgically reconstruct or restore parts of the body, such as transplanting a toe to replace a finger, but again the replaced or restored organ will not have the full functionality of the original organ.

The basic problem in the healing, replacement or repair of internal organs, such as hearts, and external organs, such as fingers, and of healing or repair of bone and skin tissues is thereby one of providing effective techniques for regenerating tissues in a manner similar to the original, embryonic growth of the tissues, thereby avoiding the development of scar tissues and the use of artificial constructs and aids.

All of the problems found in the healing or regeneration of internal organs, bone and skin tissues are found in the healing or regeneration of the nervous system and the results of injury, destruction or deficiency the nervous system have long been recognized as being as severe as for other organs of the body. The techniques for healing or regeneration nervous tissues, however, have not developed even as far as those for other organs of the body for a number of reasons. Many of these reasons arise from the nature of the nervous system. That is, the functions of the nervous system cannot be even partially restored by artificial constructs or implants and the nervous system is difficult to work upon because of the complexity and relative small physical size of the elements of the system. In addition, nervous tissue does not normally have the regenerative capabilities of other tissues of the human body and the development of effective methods and apparatus for regeneration of nervous tissue has remained a correspondingly severe problem.

The problems of regeneration of nervous system tissues, representing the most difficult case, may therefore be taken as illustrative of the problems in all forms of tissue regeneration, including the regeneration of internal organs, skin and bone. For example, the initial method for repair of nerves involved physically joining the ends of a severed or destroyed nerve by microsurgical suturing to connect the ends of the sections of a nerve into direct contact and included inserting a nerve graft between the severed ends of the nerve when necessary. This technique was not completely satisfactory, however, because of trauma to the nerve sections from the suturing, because the direct physical connection of the nerve sections frequently resulted in pressure or tension on the nerve sections and an inadequate or failed joining of the nerve, and because scar tissues frequently formed around and between the nerve endings. It should be noted that similar techniques are used, and similar problems arise, for example, in the repair or replacement of skin tissues, bone tissues and internal and external organs.

The next stage of development was the use of a nerve guide to join the ends of two sections of nerve wherein a nerve guide is a hollow tube of sufficient internal diameter to accommodate the ends of the nerve sections. The ends of the two nerve sections are inserted into the tube from either end so that the ends of the nerve sections are not in direct contact but are within an experimentally determined distance of one another, usually 5 to 10 millimeters. This method allowed better results because the suturing required to fix the nerve ends in the tube was less than that required to connect the nerve ends in the earlier method and because the tube provided some protection from extraneous tension and pressure. The nerve guide also prevents the ingrowth of fibrous scar tissue that can become interposed between the nerve endings and each nerve ending can begin growth with interference from the too close proximity of the other nerve ending. The use of the nerve guide also enhances the property of neurotrophism in the regenerating nerve tissue, wherein supportive cells called Schwann cells resident in the distal or cut end of the nerve emit neuronotrophic factors which promote and regulate the growth of the nerve tissues. In particular, it has been found that certain neuronotrophic factors are target specific and guide the growth of nerve tissue so that regenerating nerve tissues will grow to nerve tissue rather than to muscle or tendon tissues and so that motor and sensory axons will grow to join with, respectively, motor and sensory axons.

The use of nerve guides, which provided a closed environment around the injured or deficient nerves, then led to attempts to manipulate the microenvironment within the nerve guides to further enhance the healing or regenerative processes by introducing growth promoting agents into the nerve guide. The initial efforts involved inserting the agents into the nerve guide before the nerves were introduced into the guide but were not completely successful because it was found that the timing of the introduction of various agents had a significant effect on the healing or regenerative processes. That is, the too early or too late introduction of the various agents can be detrimental to the regenerative processes.

An attempt was made to provide better control over the selection and timing of the introduction of agents into the nerve guide by providing various forms of "input port" through which agents could be selectively introduced into a guide. These input ports took various forms, ranging from direct injection into the guide by means of a suitable hypodermic to the provision of a tube leading into the nerve guide or having openings into the nerve guide. While this allowed agents to be selected and introduced at times chosen to best facilitate the healing and regenerative processes, the method was again not completely successful for a number of reasons. Among these are that the successive injection of agents into a nerve guide causes pressures within the nerve guide that are detrimental to the healing and regeneration processes. The resulting pressures in a nerve guide may even result in the nerves being forced out of the guide, thereby completely disrupting the healing processing and causing yet further injury to the nerves. In addition, it is desirable to be able to remove agents from the environment within the guide as the requirements of the regenerative processes change with time and to obtain samples of the environment, thereby allowing better control of the environment in the guide. The removal of agents or samples by drawing through the input port, however, causes pressure decreases within the guide that are again detrimental to the regenerative processes and that again physically disturb the nerves.

The present invention provides a solution to these and other problems of the prior art and, in particular, the problem of an effective method and apparatus for the manipulation of the growth and regeneration of biological tissues.

SUMMARY OF THE INVENTION

The present invention provides a regeneration chamber for promoting and controlling the growth of biological tissues.

The regeneration chamber of the present invention includes a chamber enclosing and defining a volume in which biological tissues are to be grown, an input port for injecting agents for promoting and controlling the growth of the biological tissues into the chamber, and an output port for pressure release and for removing agents and biological tissue growth byproducts from the chamber. The input port and chamber have at least one input passage therebetween for the flow of agents from the input port into the chamber and the output port and chamber have at least one output passage therebetween for the flow of agents and biological growth byproducts from the chamber into the output port. The provision of input and output ports thereby prevent pressure increases or decreases upon injecting agents into the chamber or upon extracting agents and biological growth byproducts from the chamber by providing flow paths for the equalization of pressures and allow superior control of the biological growth process by allowing more complete control of the microenvironment in the chamber.

In a preferred embodiment, the input passages and the output passages of the chamber are respectively proportioned to reduce increases and decreases in pressure in the chamber arising from differential flow rates of agents and biological growth by products through the input and output passages. In further embodiments of the invention, improved flow and pressure control is accomplished by providing a plurality of input ports and output ports. In yet further embodiments, particularly those having a plurality of input ports and/or output ports, still greater control of agent and by product flow is accomplished by proportioning at least selected ones of the input passages and the output passages the input passages to the flow characteristics of certain of the agents. In certain implementations the flow characteristics of the input and output passages are controlled by selection of the materials for the chamber and input and output ports.

The regeneration chamber may further include a plurality of chamber internal structures for promoting and regulation the growth of biological tissues in the chamber. The chamber internal structures may include one or more surface matrices of agents disposed within the chamber or one or more sub-chamber for the growth of biological tissues therein and certain of the sub-chambers may be provided with input and output ports. In certain configurations the chamber internal structures comprise a plurality of subchambers, input ports, output ports and surface matrices of agents replicating selected internal biological structures of an organ to be grown.

DESCRIPTION OF THE DRAWINGS

The foregoing and other objects, features and advantages of the present invention will be apparent from the following description of the invention and embodiments thereof, as illustrated in the accompanying figures, wherein.

DESCRIPTION OF EMBODIMENTS OF THE INVENTION

As described above, the present invention provides a method and apparatus for establishing, manipulating and controlling a microenvironment around biological tissues for the purpose of enhancing and controlling the regeneration of the biological tissues. In certain instances the regeneration process will require establishing a microenvironment in which the inherent capabilities of the tissues are promoted and enhanced, but without undesirable effects, such as the formation of scar tissues. In other instances, for example wherein the tissues normally have little or no capacity for regeneration, the process may require the establishment of an embryonic state in the microenvironment by providing the appropriate biological triggers. The embryonic state will, in turn, restore the embryonic pluripotential capability of the tissues, that is, the capability of undifferentiated cells to grow specialized cells, such as nerve axon cells, as guided by the local microenvironment and thereby regenerating missing, damaged or destroyed cells, such as nerve fibers.

The following will first describe the present invention as embodied for the growth and regeneration of the tissues of the nervous system, as representing the most difficult case with for the regeneration of tissues, and then will describe modifications of the described embodiment for the growth and regeneration of other tissues.

A. Structure and Operation (FIGS. 1A, 1B and 1C)

1. General Structure and Operation

Figure 1A:
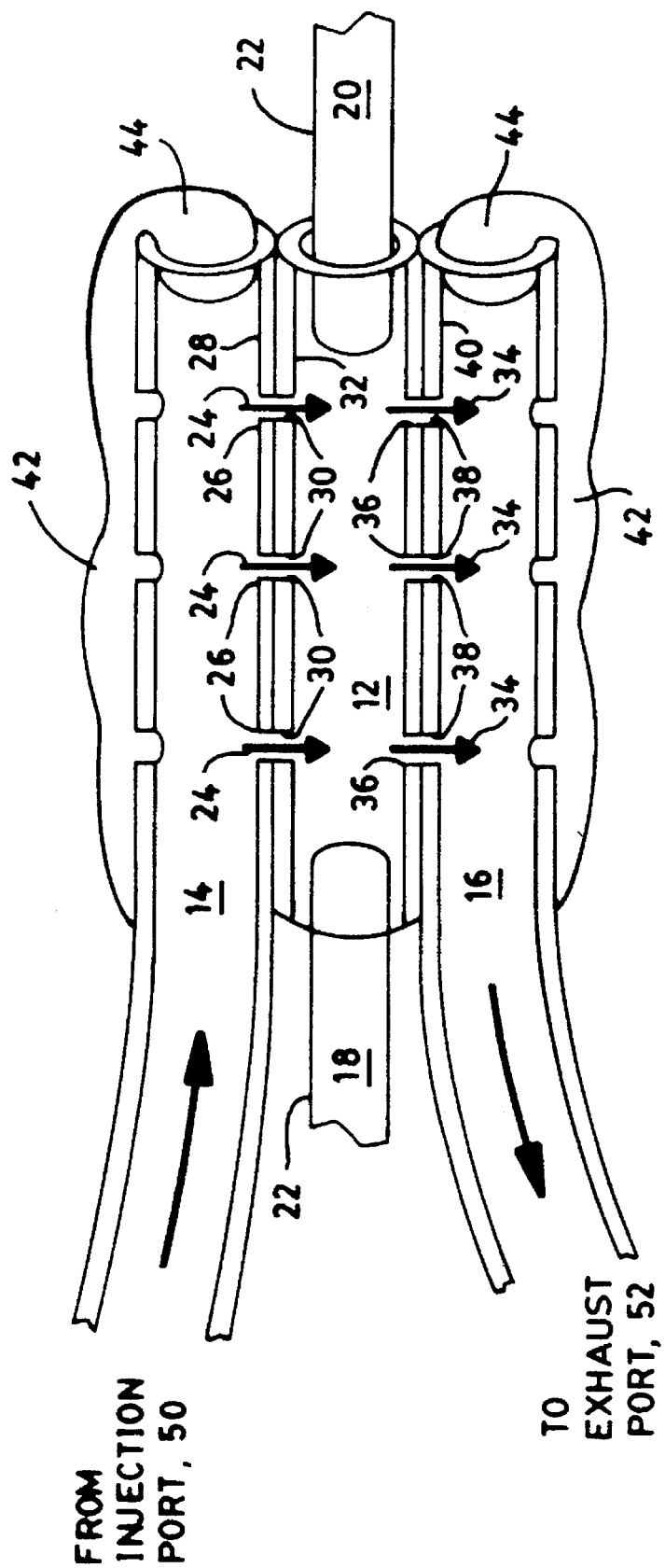
FIG. 1A is a diagrammatic representation of a regeneration chamber.
Figure 1B:
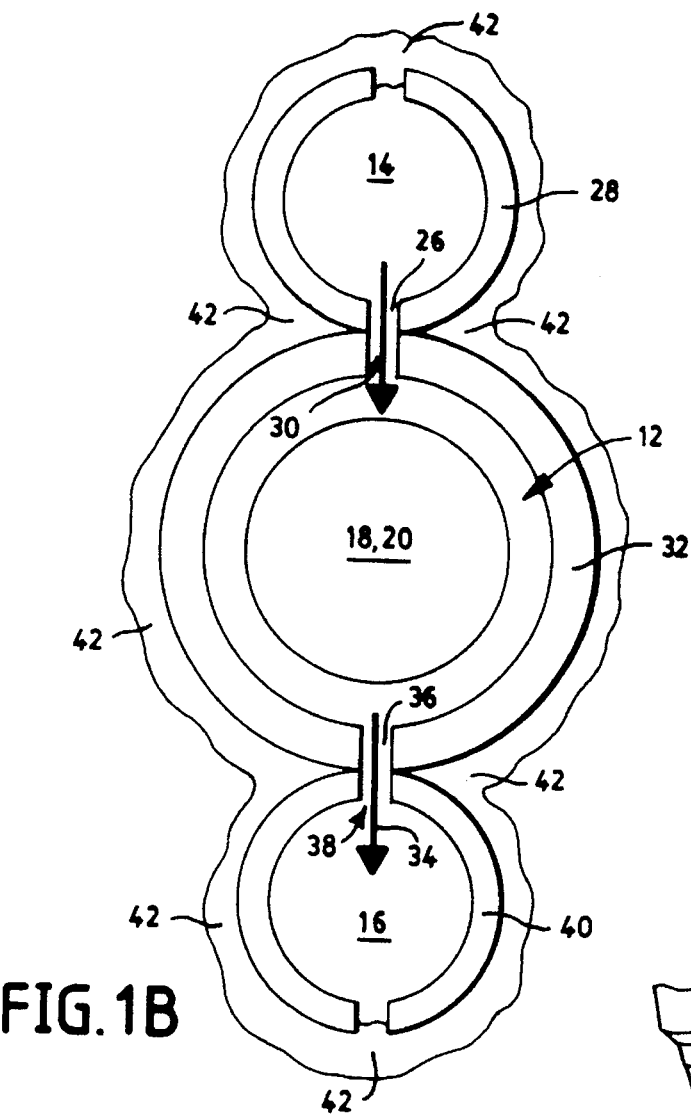
FIG. 1B is a cross section view of a regeneration chamber.
Figure 1C:
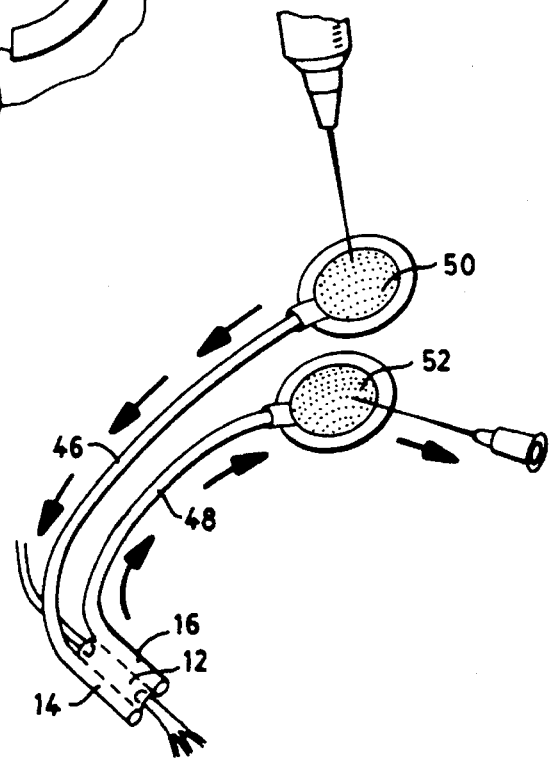
FIG. 1C is a diagrammatic representation of the injection ports and exhaust ports of a regeneration chamber.

Referring to FIGS. 1A and 1B, therein are respectively represented diagrammatic and cross section views of a Regeneration Chamber 10 of the present invention as implemented for the regeneration of a peripheral nerve, such as may be found in a hand or the arm.

As shown, the basic structure of a Regeneration Chamber 10 includes a Chamber 12, an Input Port 14 and an Output Port 16 with Input Port 14 and Output Port 16 being interconnected with Chamber 12 in those portions of Chamber 12 in which the regeneration or growth process is to be executed so as to allow the flow of agents from Input Port 14 and into Chamber 12 and out of Chamber 12 through Output Port 16. As represented, Chamber 12 is shaped and dimensioned to contain the biological tissues whose microenvironment is to be controlled and, in this instance, forms a tubular chamber closely surrounding and enclosing Proximal End 18 and Distal End 20 of a generally cylindrical Nerve 22. Input Port 14 and Output Port 16 are similarly tubular in cross section and are affixed to Chamber 12 so as to lie alongside and interconnect with Chamber 12 along the length of Chamber 12 in at least the area between Proximal End 18 and Distal End 20.

In this implementation, Input Port 14 is interconnected with Chamber 12 by Chamber Input Passages 24 comprised of Passages 26 extending through Port Wall 28 of Input Port 14 and Passages 30 extending through Chamber Wall 32 wherein Passages 26 and 30 are aligned and oriented to intersect to allow the passage of agents through Input Port 14 and into Chamber 12. In a like manner, Chamber 12 is interconnected with Output Port 16 by Chamber Output Passages 34 comprised of Passages 36 extending through Chamber Wall 32 and Passages 38 extending through Port Wall 40 of Output Port 16 wherein Passages 36 and 38 are aligned and oriented to intersect to allow the passage of agents from Chamber 12 and into Output Port 16.

Chamber 12 thereby provides an enclosed microenvironment surrounding the tissues to be regenerated while Input Port 14 provides a flow path through which various agents may be injected into Chamber 12. Output Port 16 in turn provides a flow path through which agents and the byproducts of regeneration may be extracted from Chamber 12, for example, to extract samples to evaluate the progress of regeneration or to extract agents which may superfluous or detrimental to the regeneration process at subsequent points in the regeneration process.

The exit flow path through Output Port 16 further provides a pressure relief path which allows agents and other substances in Chamber 12 to flow from Chamber 12 and through Output Port 16 when the pressure in Chamber 12 increases. The pressure in Chamber 12 may increase, for example, when new agents are injected through Input Port 14 or because of the accumulation of byproducts from the regeneration process. Output Port 16 thereby prevents the occurrence of pressures within Chamber 12 that would be detrimental to the healing and regeneration processes or possibly even force Proximal End 18 or Distal End 20 of Nerve 22 out of Chamber 12.

Output Port 16 further allows agents and samples to be extracted from Chamber 12 without incurring the detrimental pressure decreases that would occur in Chamber 12 if agents and samples were to be extracted through a single port, such as Input Port 14. In this instance, Input Port 14 is available to allow replacement fluids, such as agents, are free to flow into Chamber 12 through Input Port 14 as agents or samples are extracted through Output Port 16.

Finally, Input Port 14 and Output Port 16 may be used for these purposes either in passive combination or in active combination. In one instance of the passive combination, agents are actively injected through Input Port 14 and the resulting slight pressure increase in Chamber 12 causes displaced agents and by products to passively flow out of Output Port 16, thereby maintaining a uniform pressure in Chamber 12. In another instance of the passive combination, material is drawn from Chamber 12 through Output Port 16 by actively decreasing the pressure on Output Port 16. The resulting slight decrease in pressure in Chamber 12 will cause agents or replacement materials to passively flow into Chamber 12 from Input Port 14, thereby maintaining a uniform pressure in Chamber 12. In the active combination, agents are actively injected into Input Port 14 and, at the same time, the pressure on Output Port 16 is reduced, thereby causing a flow into Input Port 14, through Chamber 12 and out Output Port 16, again maintaining a uniform pressure in Chamber 12.

2. Materials, Regeneration Agents and Fabrication

The materials from which Chamber 12, Input Port 14 and Output Port 16 are fabricated and the dimensions and relationships between Chamber 12, Input Port 14, Output Port 16 and Passages 26, 30, 36 and 38 are determined by a multiplicity of factors.

These factors include the biological requirements for implantation in a living body and the mechanical requirements imposed by the requirement that a Regeneration Chamber 10 operate in a moving body. For example, the materials must be selected so as not to be rejected by the body and thus must be either chemically and biologically neutral or chemically and biologically compatible with the living body. In addition, Input Port 14 and Output Port 16 generally must be flexible to adapt to the motions of the surrounding body and to handling, such as in the injection of agents, without imposing strain or pressure on the tissue being regenerated, such as the two ends of Nerve 22. Chamber 12, in turn, may be flexible or rigid, depending upon the particular circumstances, but will often be of a flexible material.

It is also necessary that at least Chamber 12 be fabricated from materials that are compatible with the agents used in the regeneration process and the byproducts of the regeneration process, that is, do not cause adverse biological, chemical or physical reactions, and that have the characteristics necessary to allow and encourage regeneration of the tissues. These characteristics are determined in part by the mechanical surface characteristics of the material and in part by the molecular characteristics of the material. While Input Port 14 and Output Port 16 may be constructed from materials different from those used for Chamber 12, but must also meet the requirement of not reacting adversely with the agents used in the regeneration process or the byproducts of the regeneration process and allowing the flow of such agents and byproducts.

Finally, Input Port 14, Passages 26, 30, 36 and 38 and Output Port 16 must be of dimensions and orientations to allow the adequate flow of agents through Input Port 14 and from Input Port 14 into Chamber 12 and to allow the adequate flow of agents and regeneration byproducts from Chamber 12 into Output Port 16 and through Output Port 16.

a. Regeneration Agents

While materials suitable for implantation in a living body are well known and understood, the agents that may be used in the regeneration process should be considered further as possibly imposing additional requirements. In general, these agents may fall within several categories of agents wherein the categories may include growth factor agents, extracellular matrixes, and cell components.

Growth factor agents are generally those agents which enhance or encourage the growth of tissues and may include embryonic tissue cells, fluid from embryonic tissue cells, tissues and genetically engineered agents, such as Nerve Growth Factor (NGF), which has been genetically cloned. Extracellular matrixes include those agents which form surrounding materials, support structures or connective tissues, such as collagen, laminin, and fibronectin, which are basement membrane components of the extracellular matrix or which provide directional clues guiding the growth or regeneration of the tissues, such as target derived neuronotrophic factors. Cell components include those agents which form components of the regenerating tissues or tissue structures associated with the regenerating tissues. Cell components used in the regeneration of nerve tissues, for example, may include Schwann cells, which comprise support cells for nerve tissues, glial cells, and fibroblasts.

In the case of nerve regeneration, therefore, the possible agents include neurite promoting factors, surface active agents, neurotrophic agents, humoral agents, and chemical agents causing or enhancing the regeneration process. Examples of such would include collagen, laminin, fibronectin, living cells including Schwann cells, glial cells, dorsal root ganglia cells, neural crest cells and neural and supportive agents. Still further examples of possible agents would include, but not be limited to, nerve growth factor (NGF), ciliary neuronotrophic factor (CNTF), motor nerve growth factor (MNGF), neural cell adhesion molecules (N-CAM), N-Cadherin, fibrin, hormones such as estrogen, testosterone, thyroid hormone, corticotropin, and insulin, catalase, acidic fibroblast growth factor (aFGF), basic fibroblast growth factor (bFGF), forskolin, glia-derived protease inhibitor (GdNPF), ganglioside GM-1, insulin-like growth factor, isaxonine, leupeptin, muscle basal lamina pyronin, and Hyaluronic Acid.

It must be noted that the above listed agents are only exemplary and representative and are not intended to be a limiting definition of the possible agents that may be used in the regeneration process and that yet further agents may be defined for each form of tissue to be regenerated.

It is therefore apparent that the possible agents and regeneration byproducts may be in liquid, viscous, gel, or semisolid form and may include cells in suspension. The dimensions and configurations of at least Input Port 14, Output Port 16 and Passages 26, 30, 36 and 38 must be selected to allow free flow of agents having a significant range of physical properties. In the instance of a Regeneration Chamber 10 having a single Input Port 14 and single Output Port 16, for example, as in the implementation represented in FIGS. 1A and 1B, the dimensions and configurations of these elements would be selected for the agent to be used which has the most difficult flow requirements, such as a gel or semisolid, thereby also providing an adequate flow path for liquid or viscous agents.

b. Materials and Fabrication

Next considering the materials from which Chamber 12, Input Port 14 and Output Port 16 may be constructed, as described above, Input Port 14 and Output Port 16 may be of a different material from Chamber 12, but the materials of Chamber 12, Input Port 14 and Output Port 16 must meet the requirements described above. The materials will include both artificial or man-made materials and natural materials, including nonabsorbable and nonabsorbable materials, non-autogenous, autogenous and autologous tissues, metals, meshes and biodegradable and non-biodegradable materials. Examples of such would include silicone, polyethylene, silastic, various polymers, PGS, PDA, PGA 2 polyglycolic acid, various biodegradable compounds, vein, inverted vein, artery, inverted artery, amnion, collagen, laminin, fibronectin, various other macromolecular protein substances, cultured cells, fetal tissues, muscle tissue, and intestine.

A Regeneration Chamber 10 having any configuration of one or more Input Ports 14, one or more Chambers 12 and one or more Outputs Port 16 may be fabricated from the above materials by a variety of methods, depending upon the configuration of the chamber and ports required for regeneration of a particular organ and the materials preferred for each application. Such methods could include extruding Input Port 14, Chamber 12 and Output Port 16 as a single element, or suturing or gluing one or more pieces of material into the required configuration, or casting or molding certain of these elements, or a combination of such methods.

It must be noted that the above listed materials and fabrication methods are only exemplary and representative and are not intended to be a limiting definition of the possible materials fabrication methods that may be used in the regeneration process and that yet further materials and methods may be defined, found or created.

c. Utilizing the Properties of Materials

It will be noted in this regard that certain of the above materials, such as vein, occurs in its natural form with a "branching" configuration, that is, as a central tube with side tubes branching off of the central tube. Such a configuration may provide a Chamber 12 with one or more Input Ports 14 and Output Ports 16 in a single unit, wherein the central tube comprises Chamber 12 and the side tubes comprise Input Ports 14 and Output Ports 16.

It will also be noted that certain of these materials contain pores or are permeable or semipermeable membranes, and that the physical structure of such materials may provide Passages 26, 30, 36 and 38 for at least some of the agents. As will be described below with regard to further embodiments of the present invention, a Regeneration Chamber 10 may be constructed with several Input Ports 14 or Output Ports 16, each of which may be constructed of a different material wherein each material is selected according to the type and physical properties of a given agent or range of agents.

Further in this respect, the material for a port may be chosen to control the rate of flow of an agent through the port. For example, the Chamber Input Passages 26 or 30 of an Input Port 14 may be drilled or molded to reduce the rate of flow of the agents to be injected through that port or the Input Port 14 may be made of a permeable or semipermeable membrane or of a material which has pores such that the flow of agents is similarly reduced. Reducing the rate of flow of the agents injected through the Input Port 14 would, in turn, reduce the possibility of pressure peaks in the Chamber 12. In other configurations, the Passages 26 or 30 from an Input Port 14 may be of relatively smaller dimensions than the Passages 36 or 38 to the corresponding Output Port 16 and the differences in flow rate through Chamber Input Passages 24 and Chamber Output Passages 34 would further reduce the possibility of pressure peaks in the Chamber 12. In a like manner, the rate of flow of agents from a Chamber 12 and into Output Port 16 may similarly controlled for the same purposes, for example, to prevent an excessive pressure drop in the Chamber 12 when samples, agents or byproducts are drawn from Chamber 12 through an Output Port 14.

Controlling the rate of flow of agents into and out of a Chamber 12 by controlling the dimensions of Chamber Input Passages 24 and Chamber Output Passages 34 in this manner permits finer control of the rate at which the agents entered or flowed through the Chamber 12. This in turn would permit finer control of the flown and relative concentration of the agents in the Chamber 12, as may be required for control of the regeneration process.

It should be noted that the above flow control effects may also be accomplished, for example, by controlling the size of the passages between the ports and chambers during manufacture as well as by exploiting the natural characteristics of the materials used to fabricate the ports and chambers.

3. Description of a Specific Embodiment

Returning to the embodiment illustrated in FIGS. 1A and 1B, Chamber 12, Input Port 14 and Output Port 16 are constructed of individual elements, each shaped and dimensioned according to the shape and dimensions of the organ to be regenerated. In the instance of a chamber for the regeneration of a peripheral nerve in the hand, for example, Chamber 12 may be 1 cm to 15 cm long and 2 mm to 3 cm in interior diameter while Input Port 14 and Output Port 16 may have an interior diameter of less than 1 mm to greater than 1 cm and may extend along Chamber 12 for the entire length of Chamber 12 in the areas containing Passages 24 and 34. In the instance of a Chamber 12 for the regeneration of a major nerve extending, for example, from the shoulder to and into the hand, the Chamber 12, Input Port 14 and Output Port 16 would be of dimensions corresponding to the nerve to be regenerated, that is, would be of a length extending from the shoulder to the hand and of a diameter determined by the diameter of the regenerated nerve. In this and similar embodiments of Chamber 12, and as described further herein, the Chamber 12 may be provided with multiple Input Ports 14 and Output Ports 16 as required for control and manipulation of the regeneration or growth process at various points or areas along the length of the nerve.

In the present example, Chamber 12, Input Port 14 and Output Port 16 has been successfully constructed from silicon tubing and has provided satisfactory results. Chamber 12, Input Port 14 and Output Port 16 may be alternately made of polyethylene tubing as polyethylene has a biologically "cleaner" and smoother surface than silicon and a lesser risk of causing inflammation in the surrounding tissues than does silicon.

Chamber 12, Input Port 14 and Output Port 16 are bound together into a single unit by adhesive, such as a silicon adhesive, and Passages 26, 30, 36 and 38 are formed by drilling through the assembly of Input Port 14, Chamber 12 and Output Port 16 along one or more diameters which intersect the interior spaces of Input Port 14, Chamber 12 and Output Port 16. The tissue to be regenerated is then enclosed in Chamber 12 and the assembly of Chamber 12, Input Port 14 and Output Port 16 is enclosed with a Layer 42 of adhesive, again such as a silicon adhesive, which further bonds the elements into a single unit and also serves to seal the Open Ends 44 of Input Port 14 and Output Port 16 and the exterior opening caused by the drilling of Passages 26, 30, 36 and 38. In addition, it has been found that the body will form a layer of tissue enclosing the chamber, thereby further binding together and sealing the elements of the chamber together and assisting in holding the nerve endings into the chamber.

Although not shown in FIGS. 1A and 1B for clarity of representation of Regeneration Chamber 10, the Proximal End 18 and Distal End 20 of Nerve 22 of the present example are held into Chamber 12 by sutures wherein the number of sutures will depend upon the dimensions of Nerve 22 and the requirement to hold Proximal End 18 and Distal End 20 in a fixed relationship to one another within Chamber 12. In the instance of relatively small nerves, such as a peripheral nerve in the hand, a single suture in each of Proximal End 18 and Distal End 20 may be sufficient, as may be Layer 42 of adhesive. In other instances, for example, the regeneration of bone, the ends of the organs which are to be joined by regeneration may be affixed into Chamber 12 by adhesives or pins. In instances wherein an entire organ or a part of an organ is to be regenerated rather than rejoined to a like organ, such as in the regeneration of an entire finger, one end of Chamber 12 is closed and Chamber 12 with Input Ports 14 and Output Ports 16 is held in position enclosing the end of the organ to be regenerated by sutures, adhesive or pins as required.

Finally, and as illustrated in FIG. 1C, agents may be provided to Input Port 14 and drawn from Output Port 16 through, respectively, Extensions 46 and 48 which are shown as connected to an Injection Port 50 and an Exhaust Port 52. Injection Port 50 and Exhaust Port 52 are commercially available components designed to provide a self sealing means allowing hypodermic injection and withdrawal of agents and samples into and from a sealed environment. Injection Ports 50 and Exhaust Ports 52 are available from Dow Corning and similar suppliers. In alternate embodiments of the present invention, function of Injection Port 50 may be performed by any of a number of known devices, such as an intravenous type drip feed system, an external pump or an embedded pump, such as an osmotic pump. Similarly, the function of Exhaust Port 52 may be performed by any of a number of known devices, such as the type external extraction pump referred to as a hemovar drain, an embedded pump, a cachment container, or by allowing the exhausted agents and byproducts to drain into the body tissues or a body cavity to be absorbed by the body.

Further in this regard, it is known that the sequence and timing of the injection of agents into Chamber 12 is significant, and even critical, to the inducement, enhancement and control of the regeneration process. In those instances wherein the sequence and timing of agents is sufficiently known to be relatively standardized, one or more Input Ports 14 may be "preloaded" with a suitably selected sequence of agents in selected quantities. This preloading may be accomplished by direct injection into an Input Port 14, an Injection Port 50 or an Extension 46 or, for example, by a embedded and preloaded osmotic pump used in place of an Injection Port 50, and a steady pressure applied to cause the sequence of agents to flow into Chamber 12.

Lastly, while the embodiment illustrated in FIGS. 1 A, 1B and 1C have shown Input Port 14 and Output Port 16 as located diametrically opposite one another across the diameter of Chamber 12, Input Ports 14 and Output Ports 14 may be located in any position with respect to one another that will provide the desired flow of agents and regeneration byproducts into and out of Chamber 12. For example, the longitudinal axes of Input Port 14 and Output Port 16 may be located at a 90 degree angle with respect to one another along the longitudinal axis of Chamber 12, rather than at the 180 degree angle shown in FIG. 1C, or may be located closely adjacent one another along the length of Chamber 12. Further examples of the structure and orientation of Input Ports 14 and Output Ports 16 will be shown in the following embodiments of Chamber 12.

B. Further Embodiments (FIGS. 2, 3, 4, 5 and 6)

Having described the basic configuration and construction of a Regeneration Chamber 10 for the example of nerve regeneration, the following will now describe further implementations of the present invention. The following implementations will generally not be directed to specific examples of organ or tissue regeneration, but will instead discuss further general aspects of the present invention that may be adapted to specific instances as will be well understood by those of skill in the art.

1. Internally Layered Agents (FIG. 2)

Figure 2:
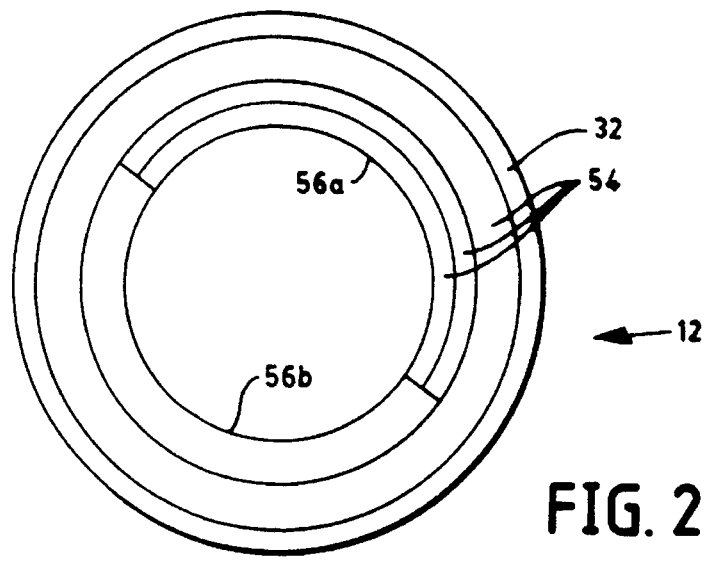
FIG. 2 is a cross sectional view of a regeneration chamber including internally layered regeneration agents.

Referring to FIG. 2, the above examples have discussed the injection of agents into a Chamber 12 through an Input Port 14. Certain of the agents, however, are of gel, semisolid or solid form or may be compounded in gel, semisolid or solid forms and are thus suitable for incorporation into a Chamber 12 as part of the internal structure of a Chamber 12 rather than being injected.

This is represented in FIG. 2, which shows a general cross sectional view of a Chamber 12 having a Wall 32 and wherein the interior of Wall 32 is provided with one or more Layers 54 of agents in gel, semisolid or solid form. Input Ports 14 and Output Ports 16 with corresponding Chamber Input Passages 24 and Chamber Output Passages 34 are not represented in FIG. 2 for clarity of representation, but Input Ports 14 and Output Ports 16 would appear generally as shown in FIG. 1B with Passages 24 and 34 extending through the walls of Input Ports 14, Output Ports 16 and Layers 54.

The agents incorporated into Layers 54 would include those described above and, in particular, various neurite promoting factors such as collagen, laninin, fibronectin, Hyaluronic Acid and other matrix components, living cells including Schwann cells, glial cells, dorsal root ganglia and various neural and supportive cell materials. For example, it is known that Schwann cells provide structural and trophic support to nerve axons and that the presence of Schwann cells in the regeneration chamber enhances the growth of axons. Schwann cells may therefore be injected into Chamber 12 as described above or, in the present implementation, may be incorporated into one or more Layers 54. In addition, matrix factors known to be necessary for the growth and proper orientation of regenerating or developing axons may be incorporated into Layers 54, or as other internal structures of Chamber 12 as described further below, to further encourage the growth of axons or nerve fibers to their appropriate distal target. The use of Layers 54 thereby allows a Chamber 12 to be constructed with a preformed inner matrix composed of specific surface active agents, living cells and humoral agents to provide the environment to enhance the repair, healing and regeneration of tissues in the Chamber 12.

It should be noted that one or more of Layers 54 may be naturally occurring layers in the material from which Wall 32 is fabricated. For example, intestine, vein, artery and muscle tissue are all complex structures which include certain of the desired agents, such as collagen. In other instances, Layers 54 may be comprised of layers bonded to Wall 32 or to other Layers 54 or may be comprised of coatings applied in the fabrication process. It should also be noted that Layers 54 are not confined to simple, successive, concentric layers, each covering the previous layers, but may have a configuration determined by the requirements of the tissue to be regenerated. For example, certain of Layers 54 may be comprised of Segments 56, so that the surface of any given Layer 54 may be comprised of two or more agents, and any Segment 56 may extend through two or more Layers 54, as is illustrated by Segments 56*a* and 56*b*.

In certain instances, it may also be preferable to construct an Input Port 14 in the same manner as the Chamber 12 of FIG. 2 so that the agents injected through the Input Port 14 would dissolve or otherwise acquire agents from the Layers 54 of the Input Port 14 and carry these agents into the Chamber 12 together with the injected agents.

2. Plural Input Ports and Output Ports (FIG. 3 and 4)

Figure 3:
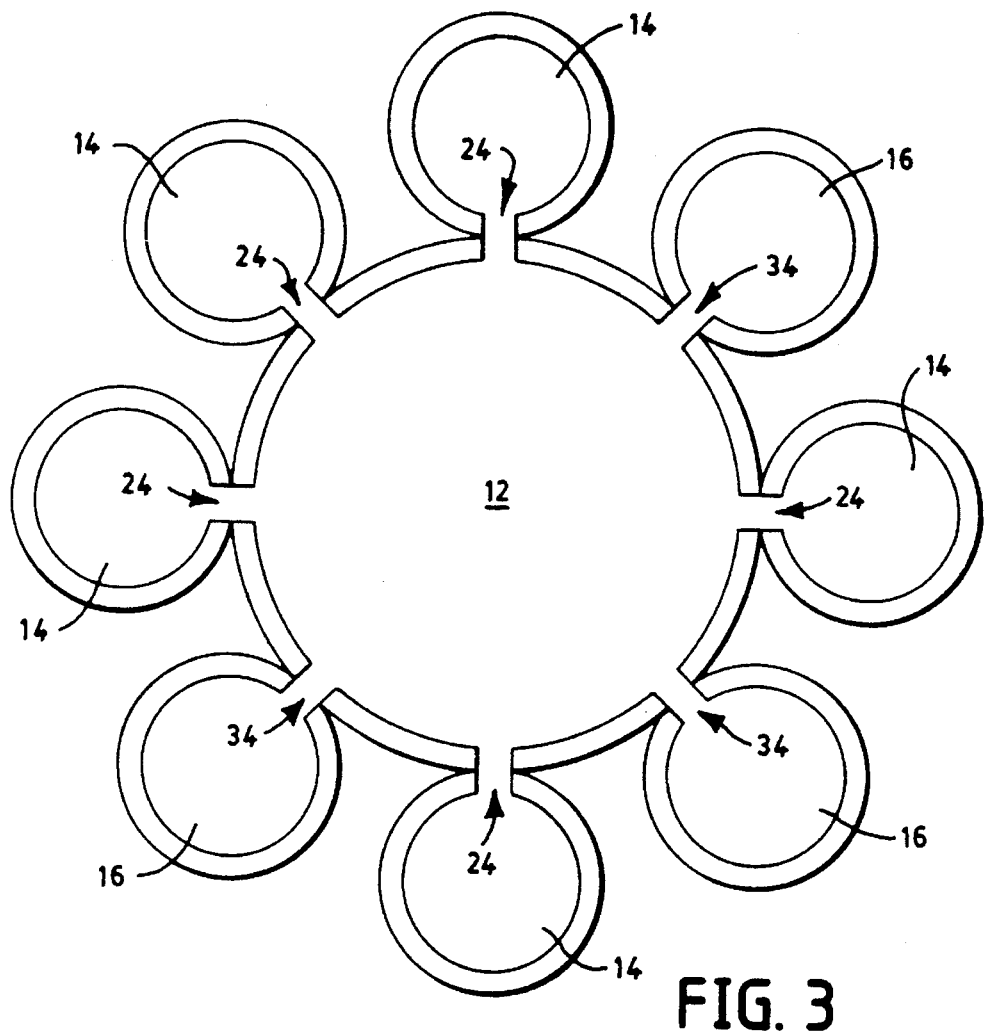
FIG. 3 is diagrammatic representation of a regeneration chamber having a plurality of input ports and output ports.

Referring to FIG. 3, it has been described above that a Chamber 12 may have one or more Input Ports 14 and one or more Output Ports 16, each of which is tailored for the injection or withdrawing of certain agents. This is illustrated in FIG. 3 wherein a Chamber 12 is provided with a plurality of Inputs Ports 14 and Output Ports 16 with corresponding Chamber Input Passages 24 and Chamber Output Passages 34.

Although Chamber 12 and Input Ports 14 and Output Ports 16 are represented in FIG. 3 as being of generally symmetric configuration, Chamber 12 would, as described, be configured according to the tissues or organ to be regenerated and could accordingly be non-symmetric in all dimensions. Input Ports 14 and Output Port 16 likewise need not be symmetrically distributed around Chamber 12 but may be distributed and of such numbers as are necessary for the desired injection of agents and extraction of agents and byproducts. For example, Chamber 12 may be of a generally elliptical or non-symmetric cross section and may vary in both width and height along axis of the chamber. In this instance, it may be desirable to distribute fewer Input Ports 14 and Output Ports 16 in those areas of Chamber 12 which are of generally thinner cross section and to provide additional ports in those areas of the chamber of greater dimensions or volume. It should be noted, in this regard, that the distribution and configuration of Input Ports 14 and Output Ports 16 according to the tissues or organ to be regenerated may also be accomplished by extending fewer Input Ports 14 and Output Ports 16 over larger portions of the Chamber 12, as well as by providing additional Input Ports 14 and Output Ports 16.

Figure 4:
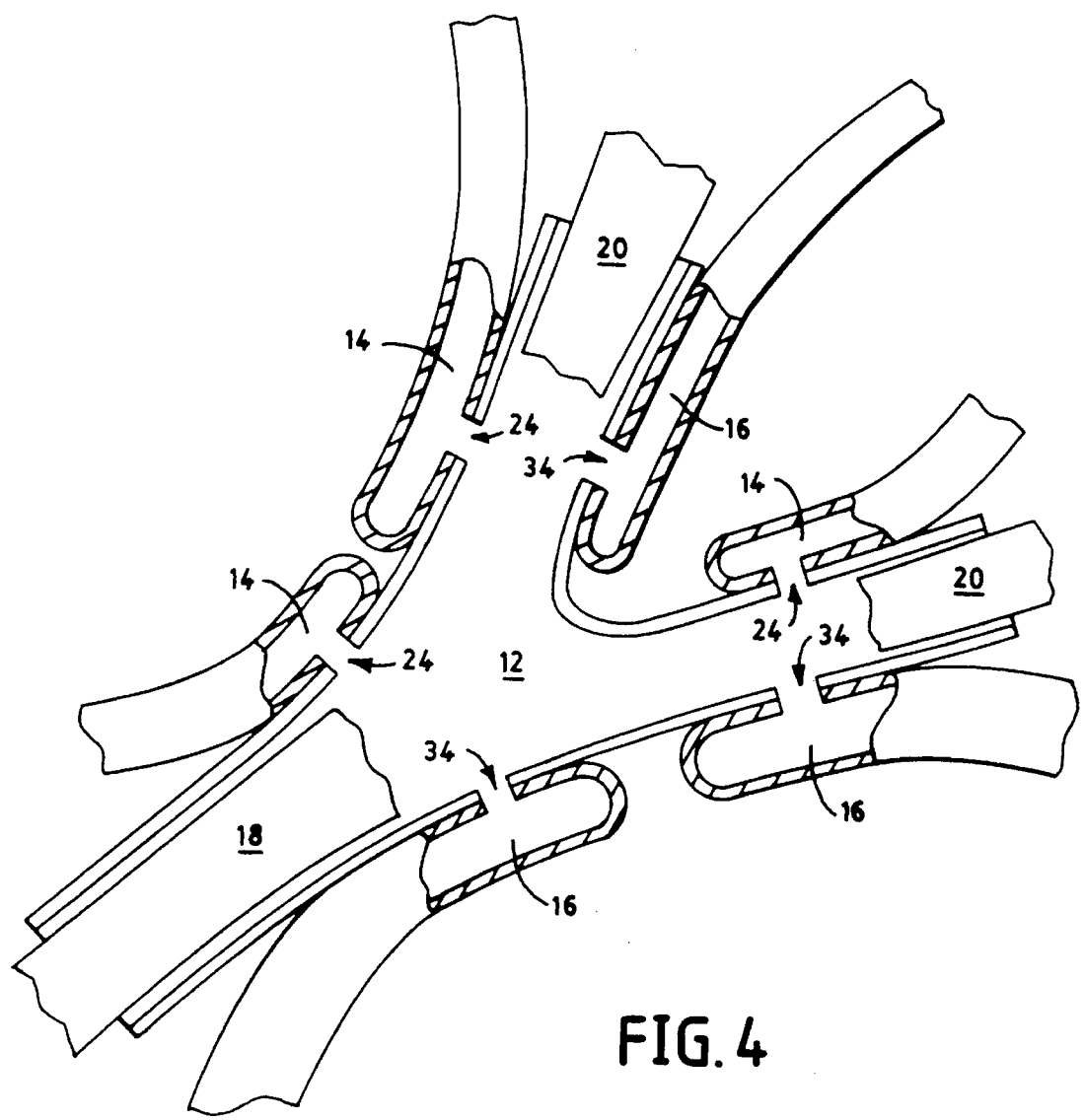
FIG. 4 is a diagrammatic representation of an embodiment of a regeneration chamber having a plurality of input ports and output ports and Y shaped distal conduits for selective distal growth.

An example of the distribution of Input Ports 14 and Output Ports 16 around a Chamber 12 shaped to enclose an organ or tissue to be regenerated is shown in FIG. 4, which illustrates a Chamber 12 shaped to regenerate a nerve at a point where the nerve branches. As shown, the Chamber 12 is Y shaped with Proximal End 18 of Nerve 22 enclosed within the vertical base of the Y shape and the two Distal Ends 20 of Nerve 22 enclosed in the two branches of the Y. Proximal End 18 may be comprised of motor or sensory nerves or a combination of motor and sensory nerves, as may be each of Distal Ends 20.

In this example, the portion of Chamber 12 enclosing Proximal End 18 is provided with one or more Input Ports 14 and one or more Output Ports 16 and the two portions of Chamber 12 enclosing Distal Ends 20 are similarly provided with one or more Input Ports 14 and one or more Output Ports 16. This configuration thereby provides superior control of the flow of agents through all parts of Chamber 12 and allows individual, specific control of the microenvironments around each of Proximal End 18 and the two Distal Ends 20. For example, if this nerve branch was comprised of the branching of a Nerve having sensory and motor axons into one Distal End 20 branch having sensory axons and the other Distal End 20 branch having motor axons, the Input Ports 14 associated with each of the Distal Ends 20 could be used to inject the appropriate neuronotrophic factors to direct growth of sensory and motor axons from Proximal End 18 to the appropriate connections with the two Distal Ends 20.

In further regard to the examples illustrated in FIGS. 3 and 4, each of Input Ports 14, Output Ports 16 and their respective Passages 24 and 34 could be further tailored for the injection and extraction of certain agents and to control the rate of flow of agents, as is generally indicated by the varying diameters of the Ports 24 and 34 illustrated in FIG. 3. Still further, Chamber 12 and certain of Input Ports 14 and Output Ports 16 may incorporate Layers 54 of agents as illustrated in FIG. 2. For example, internally layered components could be utilized for preferential directional or differential growth of axons by applying diffusable surface components to the alternate branches of the Y shaped Chamber 12 of FIG. 4.

Still further, and as has been described, it is known that the sequence and timing of the injection of agents into Chamber 12 is significant, and even critical, to the inducement, enhancement and control of the regeneration process. In those instances wherein the sequence and timing of agents is sufficiently known to be relatively standardized, one or more Input Ports 14 may be "preloaded" with a suitably selected sequence of agents in selected quantities, either by direct injection into an Input Port 14 or, for example, by a embedded and preloaded osmotic pump, and a steady pressure applied to cause the sequence of agents to flow into Chamber 12.

As has been described, a Chamber 12 with its input and output ports is configured to the shape, dimensions and structure or configuration of the tissues or organ to be regenerated. It is also well known and understood that the structure of many organs or tissues is complex and comprised of many elements, each of which may in turn comprise a complex structure. A relatively simple example of such would be shown by a cross sectional view of the interior structure of a nerve. Such a cross section shows that the nerve is comprised of one or more fascicles, each of which is comprised of several elements, numerous axons, blood vessels, and supportive and connective tissues. In many instances, therefore, the interior matrix and structure of a Chamber 12 must be structured accordingly to provide the necessary or desirable microenvironment for each element or component of the tissue or organ to be regenerated.

3. Internal Structures of a Regeneration Chamber (FIGS. 5 and 6)

Figure 5:
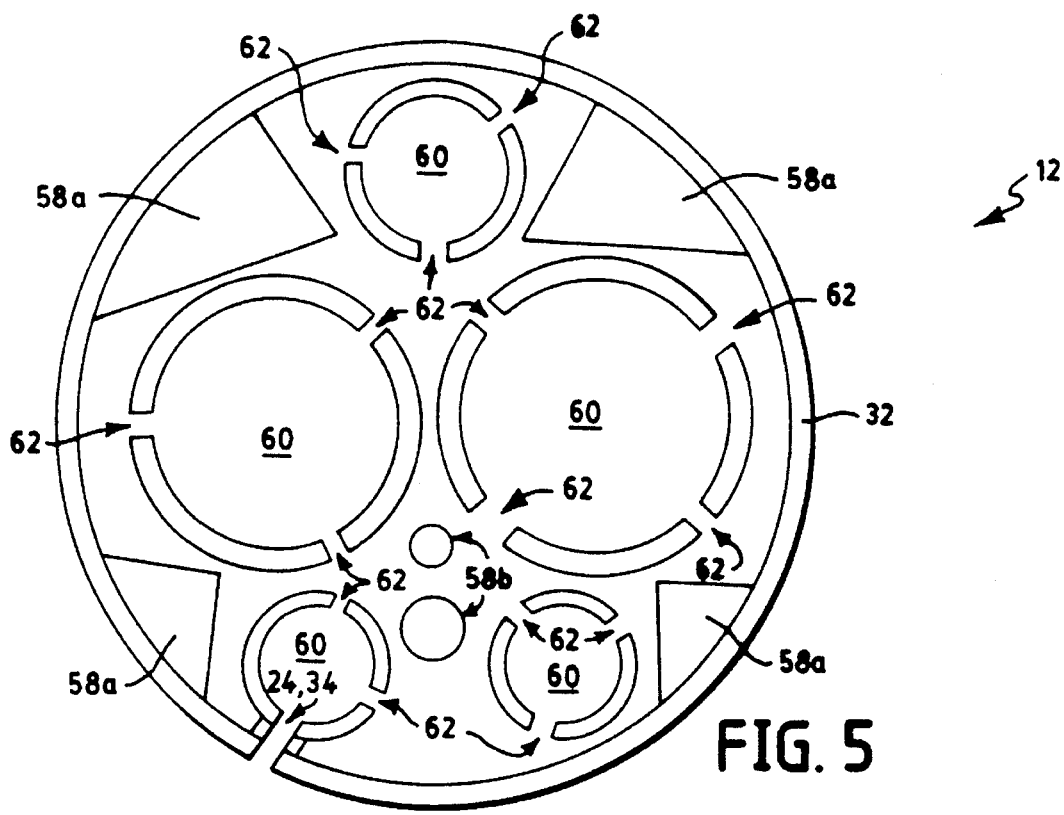
FIG. 5 is a diagrammatic, cross sectional representation of exemplary internal structures and matrices of a regeneration chamber; and, FIG. 6 is a diagrammatic, cross sectional representation of exemplary internal structures and matrices of a regeneration chamber.
Figure 6:
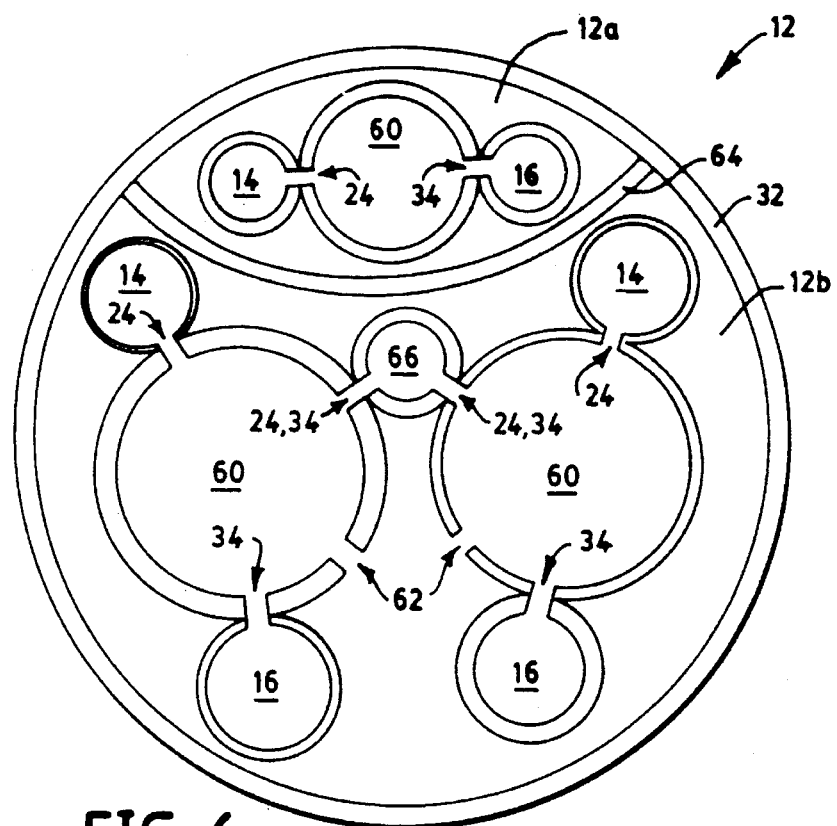

General examples of the possible features of the internal matrix and structures of a Chamber 12 to meet such requirements is illustrated in FIGS. 4 and 5 and those of skill in the relevant arts will understand how these examples may be adapted and combined for specific instances. It will be noted that the representations of Chambers 12 in FIGS. 5 and 6 do not include Input Ports 14, Output Port 16 and Passages 24 and 34 for clarity of representation but it will be understood that the Chambers 12 of FIGS. 5 and 6 will include such elements in the same manner as represented in the other Figures herein.

Referring first to FIG. 5, therein is represented a Chamber 12 having a Wall 32 wherein Wall 32 is provided with Matrix Elements 58a and 58b which may be used to shape the interior space of Chamber 12 or to provide surfaces or agents at desired locations in Chamber 12.

Matrix Elements 58a are represented as forming a part of Wall 32 of Chamber 12 while Matrix Elements 58b are not attached to Walls 32 in the same manner as Matrix Elements 58a but instead may occupy locations in the interior of Chamber 12. Matrix Elements 58b may be attached to Walls 32 at their end points, as in the manner of beams or struts running along or across a Chamber 12, or may be attached to other elements within the Chamber 12. Matrix Elements 58a and 58b may be comprised of the same material as Wall 32 and, in the instance of Matrix Elements 58a, may be formed together with Wall 32, for example, by extrusion or casting, or may be separate elements bonded to Wall 32. Matrix Elements 58a and 58b may also be comprised of agents in suitable forms, such as gels, semi-solids and solids as described with respect to FIG. 2 and, when Chamber 12 incorporates Layers 54, may be formed with or as part of the Layers 54.

The Chamber 12 of FIG. 5 is further shown as including a number of Sub-Chambers 60 which perform the same functions as Chamber 12 and which may have Passages 62 connecting the interiors of Sub-Chambers 60 to the interior space of Chamber 12. In the instance of Sub-Chambers 60 adjacent to Wall 21, these Sub-Chambers 60 may have Chamber Input Passages 24 or Chamber Output Passages 34 to Input Ports 14 and Output Port 16 around the exterior of Chamber 12. Sub-Chambers 60 may have all of the internal features herein with reference to the examples of Chamber 12, including incorporating Layers 56 and still further internal matrix and structural elements as described with regard to the Chamber 12 of FIG. 5 and Input Ports 14 and Output Ports 16 may include any or all of the features described elsewhere herein.

Referring now to FIG. 6, the Chamber 12 shown therein illustrates still further features of embodiments of Chambers 12. A Chamber 12 is represented in FIG. 6 as comprised of two Sub-Chambers 12a and 12b by a Partition 64 which may be molded or cast with Wall 32 or may be a separate component bonded to Wall 32.

While Sub-Chambers 12a and 12b may each be provided with one or more Input Ports 14 and Output Ports 16, Sub-Chambers 12a and 12b are further represented as including one or more Sub-Chambers 60, each of which is provided with one or more Input Ports 14 and Output Ports 16 connecting with the Sub-Chambers 60 through Passages 24 and 34 as described with reference to the other Figures herein. Sub-Chambers 60 may further share one or more Ports 66, wherein each shared Port 66 may comprise an Input Port 14 or an Output Port 16. Sub-Chambers 60 may further have Ports 62 connecting the interiors of Sub-Chambers 60 with the interiors of Sub-Chambers 12a and 12b. Again, Sub-Chambers 60 may have all of the internal features herein with reference to the examples of Chamber 12, including incorporating Layers 54 and still further internal matrix and structural elements as described with regard to the Chamber 12 of FIG. 4 and Input Ports 14 and Output Ports 16 may include any or all of the features described elsewhere herein.

To summarize, the internal structure and spaces defined by the general interior of a Chamber 12 define the volume in which the regeneration process is to be carried out and Chamber 12 will generally form a "mold" for the tissues to be generated. Sub-Chambers 12a and 12b and Sub-Chambers 60, together with Matrix Elements 58a and 58b and any other interior structures of a Chamber 12, as illustrated in FIGS. 5 and 6 are designed and configured according to the requirements to define interior structures of the organ or part to be regeneration. That is, the interior spaces of a Chamber 12 and of Sub-Chambers 12 and 60 within a Chamber 12 may each be individually tailored to regenerate different tissues, such axons, arteries or veins, and connective and supportive tissues, or in the case of other organs, bone, cartilage, and Biliary tract gut, to mention a few. For example, and referring to FIGS. 5 and 6, the Chamber 60 in Sub-Chamber 12a may be used to regenerate a vein or artery while the Sub-chambers 60 in Sub-Chamber 12b are used to regenerate sensory or motor axons. The remaining interior spaces of Sub-Chambers 12a and 12b may be used to regenerate the surrounding supportive and connective tissues. The Input Ports 14 and Output Port 16 illustrated in FIGS. 5 and 6, and in the other Figures, then allow the control and manipulation of the total and individual environments within these spaces to induce, promote and enhance the different tissues of the biological structure to be regenerated.

In the regeneration of an ear or a portion of a liver, for example, the primary Chamber 12 would effectively form a mold defining the shape and dimensions of the complete organ and would be provided with Input Ports 14 and Output Ports 16 as described with reference to the Figures presented herein. The interior structures defined by Sub-chambers 12 and 60 would define the shape and dimensions of the interior structures and tissues of the ear or liver to the extent necessary for successful regeneration of these parts of the organ and may be provided with individual Input Ports 14 and Output ports 16 as described herein above. In this regard, certain tissues of the biological structure may themselves be able to provide a sufficient degree of structural guidance in the regeneration process, so that it may not be necessary in such instances to fully replicate the fine internal details of the organ completely.

Another example of an application of the regeneration chamber of the present invention is the use of multiple Chambers 12, each with its own internal structures, such as may be used in the regeneration of the ball and socket joint of a hip. In this instance, one Chamber 12 would be affixed to the remaining portion of the hip structure, would have an interior of the shape and dimensions of the socket portion of the hip joint and would have and internal structure as necessary to regenerate the structure of the hip socket. A second Chamber 12 would be affixed to the upper portion of the thigh bone and would be of such shape, dimensions and interior structure to regenerate the ball portion of the hip joint.

Yet another example is the regeneration of a finger wherein the primary Chamber 12 would again define the shape and dimensions of the regenerated finger and the interior structures provided by Sub-Chambers 12 and 60 would again replicate the inner structures of the finger, such as the bones, blood vessels and nerves, to the extent necessary. This example illustrates another factor in the general application of the regeneration chamber of the present invention in that certain parts of the body may contain discontinuous elements, such as the bones of the finger. In such instances, there could be a separate Chamber 60 for each bone in the portion of the finger to be regenerated, each such Chamber 60 having a shape and dimensions to form a mold to the bone to be regenerated therein and with the Chambers 60 positioned within the Chamber 12 in the locations occupied by the bones in the regenerated finger.

This last example, illustrates yet another factor in the application of the present invention to the regeneration of more complex structures in that, in many instances the regeneration chamber includes a portion of already existing tissues which are to be regenerated, such as Proximal End 18 of Nerve 22. In such instances the existing tissues will serve as a promoter or "seed" for the initiation or the regeneration process, which essentially involves the growth of new portions of the existing tissues. In other instances, for example, the growing of entirely new bones in a finger which is to be regenerated, it may be necessary to "seed" the chamber with a living or non-living embryonic sample of the tissue to be grown, or with an artificial construct which would serve this purpose. In yet other instances, it may be possible to substitute an entire artificial construct rather than growing the tissues. In these instances the growth "seed" or artificial construct would be incorporated into the appropriate chamber in the manner described herein.

Finally, it may be preferable in many instances to use bio-degradable or bio-absorbable materials for at least some of the internal structures of a Chamber 12 and of Sub-Chambers 12 and 60, including the Input Ports 14 and Output Ports 16 of Sub-Chambers 12 and 60, when it is undesirable for such internal structures to remain embedded in the completed organ or tissues.

The internal structure of a Chamber 12 and the Input Ports 14 and Output Ports 16 of the Chamber 12 and Sub-Chambers 60 may therefore be generally designed and configured according to the structure of the organ or tissue to be regenerated, repaired or healed and as such assumes a form reflecting the structure of that organ or tissue. As described, the level of detail at which the internal structure of a Chamber 12 replicates the internal structure of the biological structure to be regenerated depends in part upon the biological structure itself. In certain instances, such as a peripheral nerve, the tissues of the biological structure may themselves be able to provide a sufficient degree of structural guidance in the regeneration process. In other instances, such as the regeneration of a finger, it may be necessary to replicate at least major components of the biological structure while relying upon the soft tissue components, such as certain of the peripheral nerves, to provide guidance for their own regeneration.

A Regeneration Chamber 10 of the present invention may therefore be used to regenerate, heal or repair virtually any biological structure, including nerves, the spinal cord and portions of the brain, internal organs, bone structure, fingers, ears and skin. The specific structure and configuration of the Regeneration Chamber 10 will, in each instance, be determined by the biological structure being regenerated, ranging from the relatively simple configuration of FIG. 1 for peripheral nerves to the more complex structures of FIGS. 3, 4, 5 and 6 wherein Chamber 12 essentially forms a mold for the organ or biological structure being regenerated and the interior structures and matrices of the Chamber 12 replicate at least the principle tissue structures of the organ or biological structure.

The above completes a description of presently preferred embodiments of the present invention. It will be noted that the invention described above may be embodied in yet other specific forms without departing from the essential characteristics thereof. Thus, the present embodiments are to be considered in all respects as illustrative and not restrictive, the scope of the present invention being indicated by the appended claims rather than by the foregoing description, and all changes and modifications which come within the meaning and range of equivalency of the claims are therefore intended to be embraced therein.

What is claimed is:

1. A regeneration chamber for promoting and controlling the growth of nerve tissues, comprising:

a chamber enclosing and defining a volume in which nerve tissues are to be grown, at least one input port for injecting at least one agent for promoting and controlling the growth of the nerve tissues into the chamber, and at least one output port for removing the at least one agent and nerve tissue growth byproducts from the chamber, the at least one input port and the chamber having at least one input passage there between for the flow of the at least one agent from the at least one input port into the chamber, and the at least one output port and the chamber having at least one output passage there between for the flow of the at least one agent and the nerve tissue growth byproducts from the chamber into the at least output port, wherein the at least one input port and the at least one output port are operative during the growth of the nerve tissue for the flow of the at least one agent from the at least one input port into the chamber and the flow of the at least one agent and the nerve tissue growth byproducts from the chamber and into the at least one output port at any selectable time during the growth of the nerve tissue.

2. The regeneration chamber of claim 1, further including a plurality of input ports.

3. The regeneration chamber of claim 1, further including a plurality of output ports.

4. The regeneration chamber of claim 1 wherein the chamber further comprises a plurality of chamber internal structures, the chamber internal structures comprise one or more surface matrices of agents disposed within the chamber.

5. The generation chamber of claim 1 wherein the the at least one agent is selected from the group of agents including embryonic tissue cells, fluid from embryonic tissue cells, Nerve Growth Factor (NGF), collagen, laminin, and fibronectin, target derived neuronotropic factors, Schwann cells, glial cells, dorsal root ganglia cells, neural crest cells, ciliary neuronotropic factor (CNTF), motor nerve growth factor (MNGF), neural cell adhesion molecules (N-CAM), N-Cadherin, fibrin, estrogen, testosterone, thyroid hormone, corticotropin, and insulin, catalase, acidic fibroblast growth factor (aFGF), basic fibroblast growth factor (bFGF), forskolin, glia-derived protease inhibitor (GdNPF), ganglioside GM-1, insulin-like growth factor, isaxonine, leupeptin, muscle basal lamina pyronin, and Hyaluronic Acid.

6. The generation chamber of claim 1 wherein the nerve tisues are the tissues of peripheral nerves.

\* \* \* \* \*